(12) United States Patent
Chung et al.

(10) Patent No.: US 11,028,437 B2
(45) Date of Patent: Jun. 8, 2021

(54) METHOD FOR EVALUATING THE RISK OF DRUG HYPERSENSITIVITY REACTION INDUCED BY SULFAMETHOXAZOLE AND TRIMETHOPRIM

(71) Applicant: Chang Gung Memorial Hospital, Linkou, Taoyuan (TW)

(72) Inventors: Wen-Hung Chung, Taoyuan (TW); Shuen-Iu Hung, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 27 days.

(21) Appl. No.: 16/374,651

(22) Filed: Apr. 3, 2019

(65) Prior Publication Data
US 2019/0226023 A1 Jul. 25, 2019

Related U.S. Application Data

(63) Continuation of application No. PCT/CN2016/103537, filed on Oct. 27, 2016.

(51) Int. Cl.
*C12Q 1/6874* (2018.01)
*C12Q 1/02* (2006.01)
*C12Q 1/6883* (2018.01)

(52) U.S. Cl.
CPC ........... *C12Q 1/6874* (2013.01); *C12Q 1/025* (2013.01); *C12Q 1/6883* (2013.01); *C12Q 2600/106* (2013.01); *C12Q 2600/156* (2013.01); *C12Q 2600/166* (2013.01); *C12Q 2600/172* (2013.01)

(58) Field of Classification Search
None
See application file for complete search history.

(56) References Cited

U.S. PATENT DOCUMENTS

| 2012/0238455 A1 | 9/2012 | Nakamura et al. |
| 2015/0218634 A1 | 8/2015 | Zhang et al. |

FOREIGN PATENT DOCUMENTS

| CN | 1209317 A | 3/1999 |
| CN | 103173538 A | 6/2013 |
| CN | 104450912 A | 3/2015 |
| JP | 2016503287 A | 2/2016 |
| WO | 0059515 A2 | 10/2000 |
| WO | 2011130152 A2 | 10/2011 |

OTHER PUBLICATIONS

Hughes, W.T. Clinical Infectious Diseases. 1998. 27: 191-204 (Year: 1998).*
Ying-Fang Lin et al., "Severe Cutaneous Adverse Reactions Related to Systemic Antibiotics," Clinical Infectious Diseases, Mar. 2014, pp. 1377-1385, vol. 58, No. 10.
"Drug Interview Form Lectisol Table 25 mg" 5th A Edition, Oct. 2007, pp. 1-42.
Antibiotics Books, Sulfamethoxazole-Trimethoprim [ST], Publication date: Jul. 31, 2010, downloaded from http://www.antibiotic-books.jp/drugs/91.
Office Action for Korea Application No. 10-2019-7015031, dated Jun. 29, 2020.
Office Action for Japan Application No. 2019-522658, dated May 29, 2020.
International Search Report and Written Opinion for PCT/CN2016/103537, dated Jul. 31, 2017.
Mark Jean-Aan Koh et al., "Stevens-Johnson syndrome and toxic epidermal necrolysis in Asian children," J Am Acad Dermatol, Jan. 1, 2010, pp. 54-60, vol. 62, No. 1.
Extended European Search Report for EP Application No. 16919924.7, dated Apr. 2, 2020.
Fanping Yang et al., "HLA-B*13:01 is associated with salazosulfapyridine-induced drug rash with eosinophilia and systemic symptoms in Chinese Han population," Pharmacogenomics, Aug. 2014, pp. 1,461-1,469, vol. 15, No. 11.
F.-R. Zhang et al., "HLA-B*13:01 and the Dapsone Hypersensitivity Syndrome," The New England Journal of Medicine, Oct. 24, 2013, pp. 1620-1628, vol. 369.
Esen Özkaya-Bayazit et al., "Fixed drug eruption induced by trimethoprim-sulfamethoxazole: Evidence for a link to HLA-A30 B13 Cw6 haplotype," J Am Acad Dermatol, Nov. 2001, pp. 712-717, vol. 45, No. 5.
Office Action and Search Report for Singapore Application No. 11201903679V, dated Apr. 6, 2020.
English Translation of Zimei Li, "Drug Interaction Direct Hit— Sulfonamides," Issue 1541, 2007, Pharmacist Weekly.
Office Action and Search Report mailed in corresponding TW Application No. 105134872, dated Nov. 13, 2019.

* cited by examiner

*Primary Examiner* — Carla J Myers
(74) *Attorney, Agent, or Firm* — Pilloff Passino & Cosenza LLP; Sean A. Passino; Rachel K. Pilloff

(57) ABSTRACT

Provided is a method for evaluating the risk of drug hypersensitivity reaction induced by antibiotics sulfamethoxazole and/or trimethoprim. The drug hypersensitivity reaction comprises: maculopapular eruption, fixed drug eruption, Stevens-Johnson Syndrome, toxic epidermal necrolysis, drug rash with eosinophilia and systemic symptoms. A specific HLA genotype is associated with the drug hypersensitivity reaction induced by the antibiotics sulfamethoxazole and/or trimethoprim.

3 Claims, 1 Drawing Sheet
Specification includes a Sequence Listing.

```
GCTCCCACTCCATGAGGTATTTCTACACCGCCATGTCCCGGCCCGGCCGCGGGGAGCCCCGCT
TCATCACCGTGGGCTACGTGGACGACACCCAGTTCGTGAGGTTCGACAGCGACGCCACGAGT
CCGAGGATGGCGCCCCGGGCGCCATGGATAGAGCAGGAGGGGCCGGAGTATTGGGACCGG
GAGACACAGATCTCCAAGACCAACACACAGACTTACCGAGAGAACCTGCGCACCGCGCTCCG
CTACTACAACCAGAGCGAGGCCGG
tgagtgaccccggcccggggcgcaggtcacgactccccatccccacggacggcccgggtcgccccgagtctccgggtcc
gagatccgcctccctgaggccgcgggacccgcccagaccctcgaccggcgagagccccaggcgcgtttacccggtttcat
tttcagttgaggccaaaatccccgcgggttggtcggggcggggcggggctcggggacggggctgaccgcggggccgg
ggccagg
GTCTCACATCATCCAGAGGATGTATGGCTGCGACCTGGGGCCGGACGGGCGCCTCCTCCGCG
GGCATAACCAGTTAGCCTACGACGGCAAGGATTACATCGCCCTGAACGAGGACCTGAGCTCC
TGGACCGCGGCGGACACCGCGGCTCAGATCACCCAGCTCAAGTGGGAGGCGGCCCGTGTG
GCGGAGCAGCTGAGAGCCTACCTGGAGGGCGAGTGCGTGGAGTGGCTCCGCAGATACCTG
GAGAACGGGAAGGAGACGCTGCAGCGCGCGG
```

METHOD FOR EVALUATING THE RISK OF DRUG HYPERSENSITIVITY REACTION INDUCED BY SULFAMETHOXAZOLE AND TRIMETHOPRIM

CROSS REFERENCE TO RELATED APPLICATION

This application is a continuation of PCT Application No. PCT/CN2016/103537, filed Oct. 27, 2016, the contents of which are incorporated herein by reference.

FIELD OF THE INVENTION

The present invention provides a method for evaluating the risk of drug hypersensitivity reaction, in particular the method for the risk of drug hypersensitivity reaction induced by antibiotics sulfamethoxazole (Sulfamethoxazole) and/or trimethoprim (Trimethoprim).

BACKGROUND

Drug hypersensitivity reaction has been a major clinical problem, its manifestation is very diverse, ranging from mild rash (maculopapular eruption, MPE), fixed drug eruption (FDE) to severe cutaneous adverse drug reactions (SCAR), which includes: drug rash with eosinophilia and systemic symptoms (DRESS), Stevens-Johnson syndrome (SJS) and toxic epidermal necrolysis (TEN) and so on. Drug allergies are often correlated with immune response. If a patient is allergic to a specific drug and later takes the same drug, the second exposure to the same drug elicits a faster and more severe drug hypersensitivity reaction.

Sulfamethoxazole and trimethoprim (tradenames include Baktar™ or Bactrim™, herein after referred to as Baktar) is a broad-spectrum bactericidal agent, often used to treat infections induced by *Staphylococcus, Streptococcus, Streptococcus pneumoniae, Escherichia coli*, dysentery bacteria and *Pseudomonas*, such as: respiratory tract, gastrointestinal tract, urinary tract, reproductive tract, skin, ENT, eye and oral cavity infections. There is no shortage of clinical cases of drug hypersensitivity reaction induced by Sulfamethoxazole and/or Trimethoprim, and both antibiotics are considered to be one of the common causes of SJS/TEN. Prior literature reported that HLA-B*38 is associated with sulfamethoxazole induced drug hypersensitivity reaction in European [Lonjou et al., Pharmacogenet *Genomics.*, 2008], but this association is not seen in Asian. Therefore, there remains a need to evaluate the risk of drug hypersensitivity reaction induced by sulfamethoxazole and/or trimethoprim in Asian. The present invention addresses this need.

DESCRIPTION OF THE INVENTION

The present invention provides a method for evaluating the risk of developing drug hypersensitivity induced by antibiotics sulfamethoxazole and/or trimethoprim in a patient, wherein the drug hypersensitivity reaction comprises: maculopapular eruption, fixed drug eruption and severe cutaneous adverse drug reaction. The severe cutaneous adverse drug reaction includes: Stevens-Johnson syndrome (SJS), toxic epidermal necrolysis (TEN) or drug rash with eosinophilia and systemic symptoms (DRESS). The present invention is directed to the discovery of the association of HLA-B*1301 allele and drug hypersensitivity reaction induced by antibiotics sulfamethoxazole and/or trimethoprim.

The present invention provides a method for evaluating the risk of developing a drug hypersensitivity reaction in a patient, comprising the step of detecting the presence of HLA-B*1301 allele, wherein the presence of HLA-B*1301 allele is an indicator of the risk of drug hypersensitivity reaction.

In one or more embodiments, the drug is antibiotic Baktar (sulfamethoxazole and trimethoprim).

In one or more embodiments, the drug is antibiotic sulfamethoxazole.

In one or more embodiments, the drug is antibiotic trimethoprim.

In one or more embodiments, drug hypersensitivity reaction includes but are not limited to:

maculopapular eruption, fixed drug eruption, SJS, TEN or DRESS.

The present study shows HLA-B*1301 allele does not exist those of European and African ancestry.

In one or more embodiments, the patient has the HLA-B*1301 allele.

In one or more embodiments, the patient is of Asian ancestry.

In one or more embodiments, the patient is not of European or African ancestry.

The present invention provides a reagent for detecting the HLA-B*1301 allele in the manufacture of a kit to evaluate the risk of developing a drug hypersensitivity reaction induced by antibiotics sulfamethoxazole and/or trimethoprim.

In one or more embodiments, the drug hypersensitivity reaction comprises: maculopapular eruption, fixed drug eruption, SJS, TEN or DRESS.

The presence of HLA-B*1301 allele indicates the patient has a higher than two times, higher than three times, higher than four times, higher than five times, higher than six times, higher than seven times, higher than eight times, higher than nine times, higher than ten times, higher than eleven times, higher than twelve times, higher than thirteen times, higher than fourteen times, higher than fifteen times, higher than sixteen times, higher than seventeen times, higher than eighteen times, higher than nineteen times, higher than twenty times, higher than thirty times, higher than forty times, higher than fifty times, higher than sixty times, higher than seventy times, higher than three times to seventeen times, or higher than once time to seventeen times risk of developing drug hypersensitivity reaction compared to a subject without the HLA-B*1301 allele.

Methods known in the art for detecting alleles can be used, such as (but not limited to): an oligonucleotide that specifically hybridizes to the allele, serotyping or microcytotoxicity method to determine cDNA, RNA or protein product of the allele. [Kenneth D. McClatchey. Clinical Laboratory Medicine. 2002].

In one or more embodiments, the oligonucleotide specifically hybridizes to the DNA of the peripheral blood of the patient. The oligonucleotide is designed for the most variable sequences of HLA-B*1301 allele, such as: exon 2 (SEQ ID NO: 4) and exon 3 (SEQ ID NO: 5), which are shown in FIG. 1 and SEQ ID NO 1.

In one or more embodiments, the sequences of the oligonucleotides used are: 5'-GGAGCCCCGCTTCATCACC-3'(SEQ ID NO: 2) and 5'-TCCTTGCCGTCGTAGGCTAA-3' (SEQ ID NO: 3).

In one or more embodiments, the serotyping or microcytotoxicity method is carried out on the RNA, proteins, cells or serum from peripheral blood of the patient.

The present invention provides a reagent for evaluating the risk of drug hypersensitivity reaction induced by antibiotics sulfamethoxazole and/or trimethoprim, by detecting the presence of HLA-B*1301 allele, wherein the presence of HLA-B*1301 allele indicates the risk of drug hypersensitivity reaction, and said drug hypersensitivity reaction comprises: maculopapular eruption, fixed drug eruption, SJS, TEN or DRESS.

BRIEF DESCRIPTION OF THE DRAWING

FIG. 1 shows the sequences of exon 2 (SEQ ID NO: 4) and exon 3 (SEQ ID NO: 5) of HLA-B*1301. The lowercase letters indicates the sequence of the intron (SEQ ID NO: 6) that connects exon 2 (SEQ ID NO: 4) and exon 3 (SEQ ID NO: 5). The sequence is exon 2 (SEQ ID NO: 4)-Intron (SEQ ID NO: 6)-exon 3 (SEQ ID NO: 5).

WORKING EXAMPLE

The present invention provides a method for evaluating the risk of developing a drug hypersensitivity reaction induced by antibiotics sulfamethoxazole and/or trimethoprim, the drug hypersensitivity reaction comprises: maculopapular eruption, fixed drug eruption and SCAR and said SCAR includes SJS, TEN or DRESS. The present is directed to the discovery that HLA-B allele, HLA-B*1301, is associated with drug hypersensitivity reaction induced by antibiotics sulfamethoxazole and/or trimethoprim.

In one example, 76 patients with Baktar-induced drug hypersensitivity reaction (DHR) were enrolled and their HLA typing was evaluated and compared with 482 healthy individuals. The results show 24 of the 76 patients with drug hypersensitivity reaction (SCAR, MPE or FDE) carried the HLA-B*1301 allele (31.58%). In contrast, 58 of the 482 healthy individuals carried the HLA-B*1301 allele (12.03%). Statistical analysis further indicates the presence of HLA-B*1301 allele is significantly associated with Baktar-induced drug hypersensitivity reaction (DHR vs. control: $P=4.04 \times 10^{-5}$, OR=3.37 (1.93-5.88), sensitivity: 31.58%, specificity: 87.97%) (See Table 1). In particular, the association with HLA-B*1301 allele is more significantly correlated with SCAR patients (SCAR vs. control: $P=4.52 \times 10^{-5}$, OR=17.06 (4.29-67.81), sensitivity: 70.00%, specificity: 87.97%). Based on the above results, HLA-B*1301 allele can be used to evaluate the risk of developing drug hypersensitivity reaction induced by Baktar, sulfamethoxazole or trimethoprim.

TABLE 1

HLA-B*1301 genotype analysis of 76 patients with Baktar-induced DHR and 482 healthy individuals.

| Subjects | HLA-B*13:01 N (%) | Total N | OR (95% CI) | P Value |
|---|---|---|---|---|
| DHR | 24 (31.58%) | 76 | 3.37 (1.93~5.88) | $4.04 \times 10^{-5}$ |
| SCAR | 7 (70.00%) | 10 | 17.06 (4.29~67.81) | $4.52 \times 10^{-5}$ |
| Healthy Control | 58 (12.03%) | 482 | | |

Accordingly, the present invention provides a method for evaluating drug hypersensitivity reaction in a patient after ingesting the drug, comprising the step of detecting the presence of HLA-B*1301 allele, wherein the presence of the HLA-B*1301 allele is an indicator of the risk of drug hypersensitivity reaction. The drug is antibiotic sulfamethoxazole and/or trimethoprim. Drug hypersensitivity reaction includes maculopapular eruption (MPE), fixed drug eruption (FDE), Stevens-Johnson syndrome (SJS), toxic epidermal necrolysis (TEN) and drug rash with eosinophilia and systemic symptoms (DRESS).

The preferred embodiments in the foregoing are specifically described technical features of the present invention. However, those skilled in the art can change and modify the present invention without departing from the spirit and principles of the present invention, and such changes and modifications are intended to be included within the scope of the claims listed below.

SEQUENCE LISTING

This application contains a Sequence Listing which has been submitted electronically in ASCII format and is hereby incorporated by reference in its entirety.

What is claimed is:

1. A method for treating an indication in a patient treatable by sulfamethoxazole and/or trimethoprim, comprising:

evaluating the risk of developing a drug hypersensitivity reaction caused by sulfamethoxazole and trimethoprim in a patient with an indication treatable by sulfamethoxazole and trimethoprim, comprising the step of detecting the presence of HLA-B*1301 allele from a sample from the patient, wherein the presence of the HLA-B*1301 allele indicates the patient has a higher risk of developing drug hypersensitivity reaction caused by sulfamethoxazole and trimethoprim compared to a subject without the HLA-B*1301 allele; and thereafter based on the detecting the presence of HLA-B*1301 allele from the sample from the patient, administering an antibiotic other than sulfamethoxazole and/or trimethoprim in order to minimize the risk developing a drug hypersensitivity reaction caused by sulfamethoxazole and trimethoprim, wherein said patient is of Asian ancestry and said drug hypersensitivity reaction caused by sulfamethoxazole and trimethoprim is maculopapular eruption, fixed drug eruption, Stevens-Johnson syndrome, toxic epidermal necrolysis or drug rash with eosinophilia and systemic symptoms.

2. The method according to claim 1, wherein the drug hypersensitivity reaction is a severe cutaneous adverse drug reaction.

3. The method according to claim 1, wherein the presence of HLA-B*1301 is detected in the DNA, RNA, proteins, cells or serum from the peripheral blood of the patient.

* * * * *

```
SEQUENCE LISTING

<160> NUMBER OF SEQ ID NOS: 6

<210> SEQ ID NO 1
<211> LENGTH: 791
<212> TYPE: DNA
<213> ORGANISM: Homo sapiens

<400> SEQUENCE: 1
gctcccactc catgaggtat ttctacaccg ccatgtcccg gcccggccgc ggggagcccc      60
gcttcatcac cgtgggctac gtggacgaca cccagttcgt gaggttcgac agcgacgcca     120
cgagtccgag gatggcgccc cgggcgccat ggatagagca ggaggggccg gagtattggg     180
accgggagac acagatctcc aagaccaaca cacagactta ccgagagaac ctgcgcaccg     240
cgctccgcta ctacaaccag agcgaggccg gtgagtgacc ccggcccggg gcgcaggtca     300
cgactcccca tccccacgg acggcccggg tcgcccgag tctccgggtc cgagatccgc       360
ctccctgagg ccgcggacc cgcccagacc ctcgaccggc gagagcccca ggcgcgttta      420
cccggtttca ttttcagttg aggccaaaat ccccgcgggt tggtcggggc ggggcgggc      480
```

```
tcgggggacg gggctgaccg cggggccggg gccagggtct cacatcatcc agaggatgta    540
tggctgcgac ctggggccgg acgggcgcct cctccgcggg cataaccagt tagcctacga    600
cggcaaggat tacatcgccc tgaacgagga cctgagctcc tggaccgcgg cggacaccgc    660
ggctcagatc acccagctca agtgggaggc ggcccgtgtg gcggagcagc tgagagccta    720
cctggagggc gagtgcgtgg agtggctccg cagatacctg gagaacggga aggagacgct    780
gcagcgcgcc c                                                         791

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
ggagccccgc ttcatcacc                                                  19

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tccttgccgt cgtaggctaa                                                 20

<210> SEQ ID NO 4
<211> LENGTH: 19
<212> TYPE: DNA
<213> ORGANISM: Homo sapiens

<400> SEQUENCE: 4
ggagccccgc ttcatcacc                                                  19

<210> SEQ ID NO 5
<211> LENGTH: 20
<212> TYPE: DNA
<213> ORGANISM: Homo sapiens

<400> SEQUENCE: 5
ttagcctacg acggcaagga                                                 20

<210> SEQ ID NO 6
<211> LENGTH: 244
<212> TYPE: DNA
<213> ORGANISM: Homo sapiens

<400> SEQUENCE: 6
tgagtgaccc cggcccgggg cgcaggtcac gactccccat ccccacgga cggcccgggt      60 cgccccgagt ctccgggtcc gagatccgcc ccctgaggcc gcgggacccg cccagaccct    120
cgaccggcga gagccccagg cgcgtttacc cggtttcatt ttcagttgag gccaaaatcc    180 ccgcggggttg gtcggggcgg ggcggggctc gggggacggg gctgaccgcg gggccgggc    240 cagg                                                                  244
```